(12) United States Patent
Fukano et al.

(10) Patent No.: US 8,126,110 B2
(45) Date of Patent: Feb. 28, 2012

(54) X-RAY CT SCANNER AND IMAGE CREATING METHOD

(75) Inventors: Atsushi Fukano, Otawara (JP); Shigeo Kaminaga, Otawara (JP); Hisashi Yasuda, Nasushiobara (JP); Katsuhito Morino, Utsunomiya (JP); Go Mukumoto, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/507,333

(22) Filed: Jul. 22, 2009

(65) Prior Publication Data

US 2010/0020923 A1   Jan. 28, 2010

(30) Foreign Application Priority Data

Jul. 23, 2008   (JP) .................................. 2008-189973

(51) Int. Cl.
*A61B 6/00* (2006.01)
(52) U.S. Cl. .................. 378/8; 378/4; 382/128
(58) Field of Classification Search .................. 378/4, 8, 378/19; 382/128
See application file for complete search history.

(56) References Cited

U.S. PATENT DOCUMENTS

| | | | | |
|---|---|---|---|---|
| 5,396,418 A * | 3/1995 | Heuscher | .................. | 378/15 |
| 5,687,208 A * | 11/1997 | Bae et al. | .................. | 378/8 |
| 6,188,744 B1 * | 2/2001 | Shinohara et al. | .................. | 378/8 |
| 6,236,706 B1 * | 5/2001 | Hsieh | .................. | 378/8 |
| 6,289,075 B1 * | 9/2001 | Marume | .................. | 378/8 |
| 6,337,992 B1 * | 1/2002 | Gelman | .................. | 600/425 |
| 6,496,560 B1 * | 12/2002 | Lin et al. | .................. | 378/62 |
| 7,145,982 B2 * | 12/2006 | Ikeda et al. | .................. | 378/16 |
| 7,471,757 B2 | 12/2008 | Tsukagoshi et al. | | |
| 7,684,536 B2 * | 3/2010 | Kudo | .................. | 378/8 |
| 7,912,175 B2 * | 3/2011 | Iisaku et al. | .................. | 378/8 |
| 2003/0097076 A1 * | 5/2003 | Nambu et al. | .................. | 600/504 |
| 2003/0108149 A1 * | 6/2003 | Tsuyuki | .................. | 378/54 |
| 2004/0013223 A1 * | 1/2004 | Yamazaki et al. | .................. | 378/4 |
| 2004/0114706 A1 * | 6/2004 | Ikeda et al. | .................. | 378/4 |
| 2006/0034419 A1 * | 2/2006 | Nishide et al. | .................. | 378/15 |
| 2006/0050840 A1 * | 3/2006 | Ikeda et al. | .................. | 378/8 |

FOREIGN PATENT DOCUMENTS

| | | | |
|---|---|---|---|
| CN | 1488317 A | | 4/2004 |
| JP | 06114049 A | * | 4/1994 |
| JP | 7-194588 | | 8/1995 |
| JP | 2008-48956 | | 3/2008 |

OTHER PUBLICATIONS

Office Action issued Oct. 13, 2010 in Chinese Patent Application No. 200910165161.5 (w/English language translation).

* cited by examiner

*Primary Examiner* — Alexander H Taningco
(74) *Attorney, Agent, or Firm* — Oblon, Spivak, McClelland, Maier & Neustadt, L.L.P.

(57) ABSTRACT

In an X-ray CT scanner having an X-ray tube which applies an X-ray spreading in a body axis direction of a subject, and an X-ray detector having a wide imaging range which detects the X-ray passed through the subject and converts the detected X-ray into an electric signal, a desired image creation time is set by use of a specific CT value curve in a console input unit before scanning with the X-ray. After the scanning, data of the CT value change curve is generated based on the obtained projection data. An image creation range in the generated change curve is determined based on an image creation range set in the console input unit, and the image creation is performed in the image creation unit based on the determined image creation time.

16 Claims, 5 Drawing Sheets

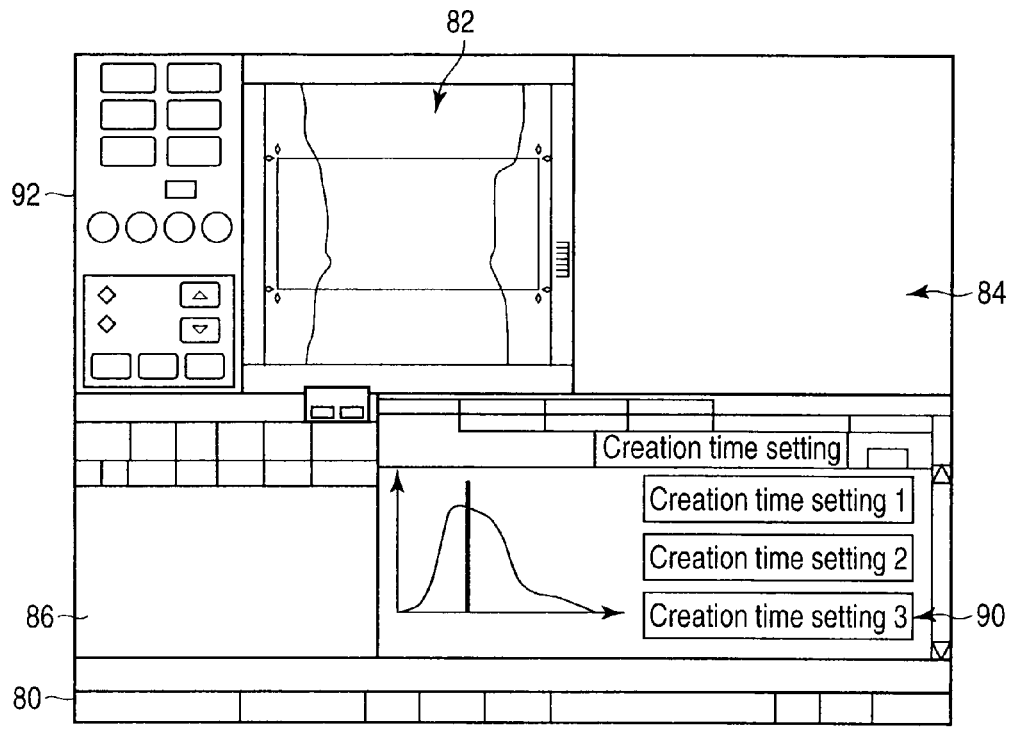
F I G. 2 A
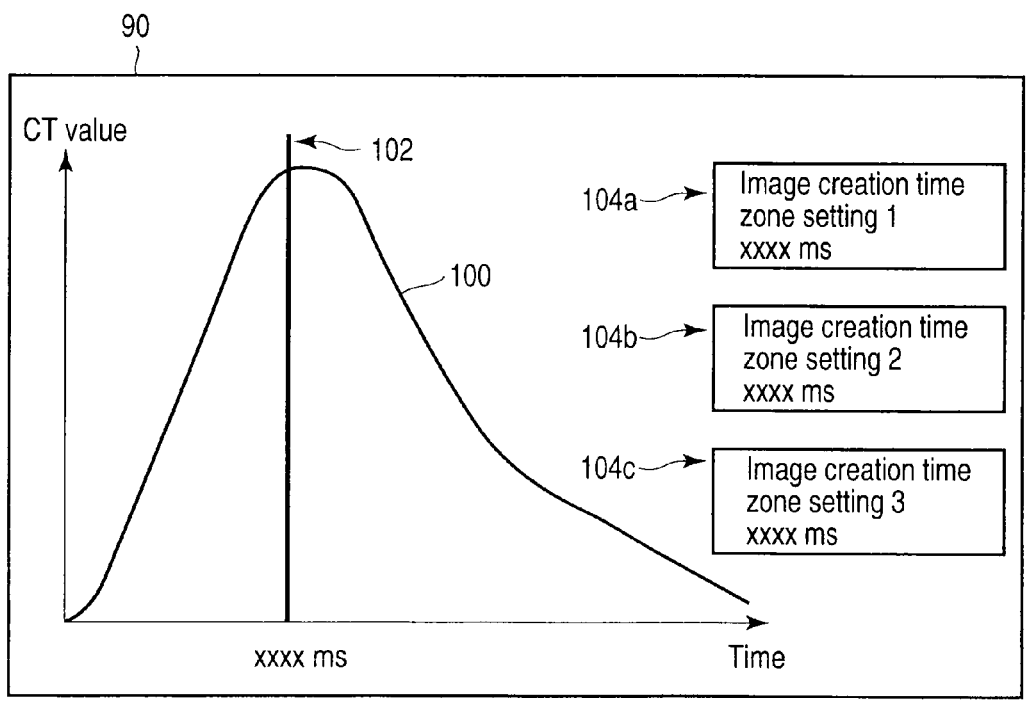
F I G. 2 B

X-RAY CT SCANNER AND IMAGE CREATING METHOD

CROSS-REFERENCE TO RELATED APPLICATIONS

This application is based upon and claims the benefit of priority from prior Japanese Patent Application No. 2008-189973, filed Jul. 23, 2008, the entire contents of which are incorporated herein by reference.

BACKGROUND OF THE INVENTION

1. Field of the Invention

The present invention relates to the field of medical equipments, and more particularly to an X-ray CT scanner used for a CT examination and an image creating method.

2. Description of the Related Art

In the technology of a conventional CT scanner, an apparatus having a wide imaging range (a large detector row) has been used. In such an X-ray CT scanner having a wide imaging range, dynamic scan that continuously scans a specific position (which will be referred to as 4D dynamic scan hereinafter) is carried out.

Further, when executing this 4D dynamic scan, it is important to perform the scan in a state where a contrast agent is sufficiently spread in a subject. Furthermore, when creating a necessary image based on this 4D dynamic scan, an operator estimates a time zone that the contrast agent reaches a test region and creates the image at this timing (see, e.g., JP-A 2008-48956 (KOKAI) and JP-A 1995-194588 (KOKAI)).

However, a judgment of estimating a time that the contrast agent reaches is difficult, and hence a created image is visually confirmed and an image in a time zone which is considered to be optimum is again created. Therefore, there is a problem that an amount of image data is enormous and a process from an examination to a diagnosis requires a large time.

Moreover, in an examination based on the 4D dynamic scan, a process from an examination to a diagnosis must be smoothly carried out. Thus, the acquisition of an image in a necessary time zone must be readily or automatically executed, and easily performing post-processing after using such an image is desired.

BRIEF SUMMARY OF THE INVENTION

It is, therefore, an object of the present invention to provide an X-ray CT scanner and an image creating method, which can set an image creation time zone in a planning stage by using a CT value change curve during scan in order to obtain an image in a necessary time zone and can sequentially automatically perform post-processing in accordance with each region after the end of scan in order to facilitate the post-processing.

That is, the present invention is characterized by an X-ray CT scanner comprising an X-ray tube which applies an X-ray which spreads in a body axis direction of a subject; an X-ray detector which detects the X-ray passed through the subject and converts the detected X-ray into an electric signal; reconfiguring section for reconfiguring an image by reconfiguring projection data detected by the X-ray detector; a display device which displays the image reconfigured by the reconfiguring section; setting section for setting an image creation time by using a pre-stored CT value change curve before applying the X-ray to perform scan; change curve acquiring section for generating data of the CT value change curve based on the obtained projection data after applying the X-ray to perform the scan; image creation range setting section for determining an image creation range in the change curve generated by the change curve acquiring section based on an image creation range set by the setting section; and image creating section for creating an image based on the image creation time determined by the image creation range setting section.

According to another aspect of the invention, there is provided an image creating method comprising:

setting an image creation time by using a pre-stored CT value change curve, and determining a position where a CT value is to be monitored;

performing scan to acquire a CT value change curve obtained after the scan, based on a CT value measured at the position;

performing fitting processing between the CT value change curve obtained after the scan and the pre-stored CT value change curve, thereby specifying the set image creation time; and creating an image corresponding to the specified image creation time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a view showing an example of a display screen of a display device 70 depicted in FIG. 1 and FIG. 2B is a view showing an example of a dialog for setting planned times as an example of a 4D scan wizard screen 90 depicted in FIG. 2A;

DETAILED DESCRIPTION OF THE INVENTION

An embodiment according to the present invention will now be described hereinafter with reference to the accompanying drawings.

Figure 1:
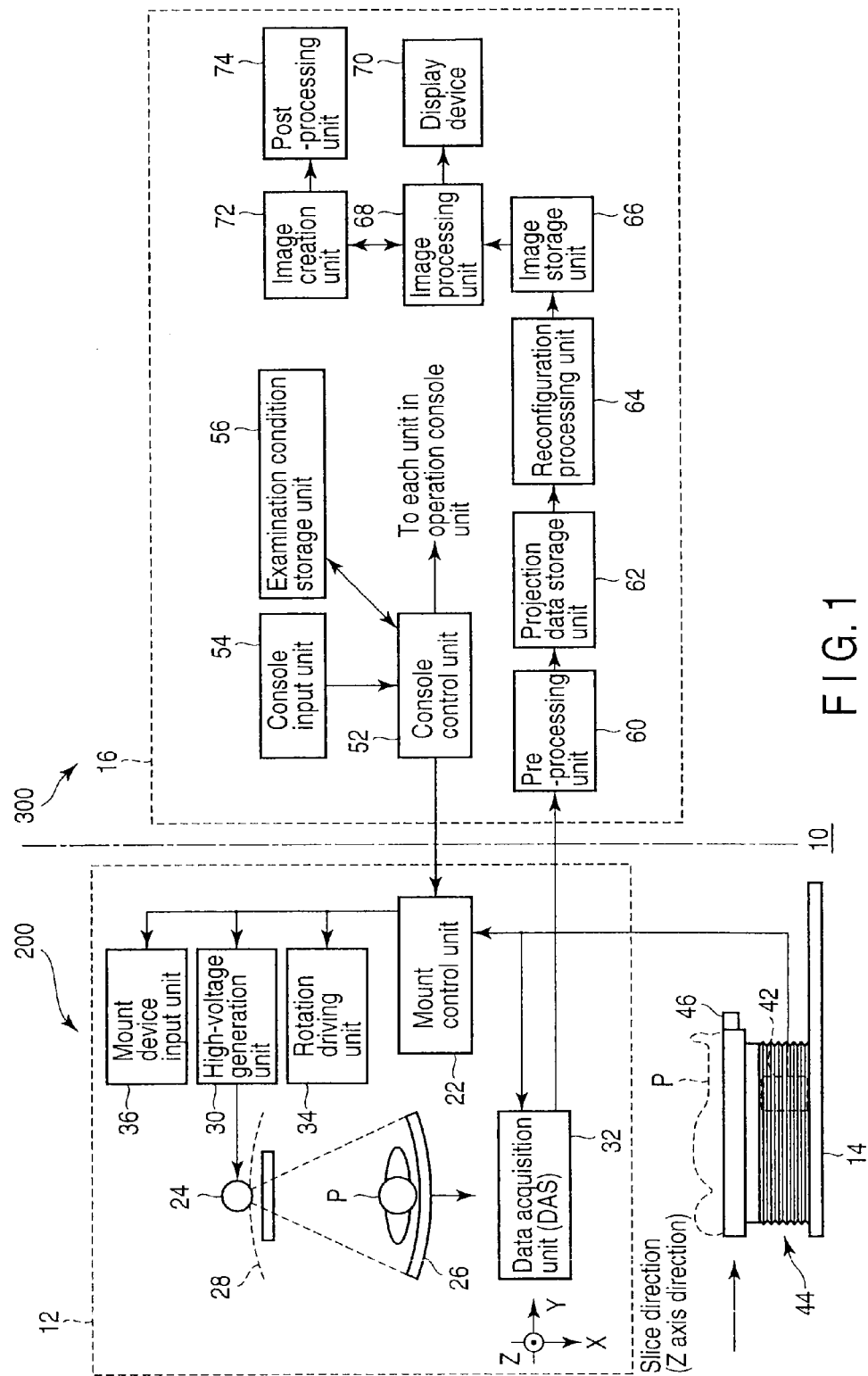
FIG. 1 is a block diagram showing an entire configuration of an X-ray CT scanner according to an embodiment of the present invention.

FIG. 1 is a block diagram showing an entire configuration of an X-ray CT scanner according to an embodiment of the present invention.

In FIG. 1, an X-ray CT scanner 10 according to this embodiment includes a mount device 12, a bed device 14, and an operation console unit 16.

The mount device 12 is constituted of a mount control unit 22, an X-ray tube 24, an X-ray detector 26, a rotation mount 28, a high-voltage generation unit 30, a data acquisition unit (DAS) 32, a rotation driving unit 34, and a mount device input unit 36, and it is installed in an examination room 200.

Further, the bed device 14 has a bed driving unit 42, a bed base 44, and a bed top panel 46. The bed device 14 is installed together with the mount device 12 in the examination room 200.

On the other hand, the operation console unit 16 has a console control unit 52, a console input unit 54, an examination condition storage unit 56, a pre-processing unit 60, a projection data storage unit 62, a reconfiguration processing unit 64, an image storage unit 66, an image processing unit 68, a display device 70, an image creation unit 72, and a post-processing unit 74. This scan console unit 16 is installed in an operation room 300.

The console control unit 52 controls the respective units in the operation console unit 16, and the console control unit 52 and the console input unit 54 constitute setting means. The console input unit 54 is formed of, e.g., a mouse or a keyboard as a first input unit.

When performing scan based on helical scan, the mount control unit 22 stores (selects examination conditions) helical scan conditions such as a slice thickness or a rotation speed input from the console input unit 54 in the examination condition storage unit 56. Further, a rotation speed, a slice thickness, or a fan angle in these conditions is output as a mount/bed control signal to the mount control unit 22 and the bed driving unit 42.

Furthermore, upon receiving an input (information concerning the selected examination conditions) from the mount device input unit 36, the mount control unit 22 outputs an X-ray beam generation control signal that controls generation of an X-ray beam to the high-voltage generation unit 30. Moreover, the mount control unit 22 outputs a detection control signal indicative of a timing for detection of the X-ray beam to the data acquisition unit 32.

The mount device input unit 36 is constituted of a display panel having a touch-sensitive function installed in the form of an "operation panel" on a surface of the mount device 12 as a second input unit. Patient identifying information such as a patient ID is input to a third input unit (not shown) provided on this display panel. Additionally, a network is used to display patient information associated with the input patient identifying information in the display panel.

Further, after setting a subject P onto the mount device 12 and selecting examination conditions by the console input unit 54 are terminated, a signal transmitted from the bed device 14 or the console input unit 54 triggers enabling input of data to the mount device input unit 36. At this time, it is desirable for the bed device input unit 36 itself to be lighted so that an examiner can recognize that input is possible.

Furthermore, a detection unit (not shown) which detects that the examiner has entered the operation room 300 may be provided on, e.g., a door (a door that partitions the examination room 200 and the operation room 300) of the operation room. The mount control unit 22 may be configured to avoid enabling input of data to the mount device input unit 36 until it receives information that this detector has detected entrance of the examiner into the operation room 300. When such a configuration is adopted, since scan (application of an X-ray) is performed with respect to the subject P in a state where movement of the examiner into the operation room 300 from the examination room 200 has been detected, the examiner can be avoided from excessive radiation exposure.

It is to be noted that the detection unit is provided, e.g., near the door and constituted of one detection unit provided in the examination room 200 and the other detection unit provided in the operation room 300. Moreover, when the one detection unit detects the examiner and then the other detection unit detects the examiner, movement of the examiner into the operation room 300 from the examination room 200 is detected.

The high-voltage generation unit 30 supplies to the X-ray tube 24 a high voltage required to emit an X-ray beam from the X-ray tube 24 in accordance with a control signal from the mount control unit 22. The X-ray tube 24 emits an X-ray beam by using the high voltage supplied from the high-voltage generation unit 30. The X-ray beam emitted from the X-ray tube 24 is a beam having a fan shape or a cone shape.

The X-ray detector 26 detects the X-ray beam which has been emitted from the X-ray tube 24 and passed through the subject P. In case of a single-slice CT scanner, the X-ray detector 26 is constituted by laying X-ray detection elements of, e.g., 1000 channels out in a fan-like pattern or a linear pattern. Additionally, in case of a multi-slice CT scanner, the X-ray detector 26 is constituted by arranging a plurality of X-ray detection elements in two directions orthogonal to each other (a slice direction and a channel direction) like an array, thereby forming a two-dimensional X-ray detector.

The rotation mount (a gantry) 28 holds the X-ray tube 24 and the X-ray detector 26 therein. Further, the rotation mount 28 is rotated on a rotary axis running through an intermediate point of the X-ray tube 24 and the X-ray detector 26 by the rotation driving unit 34.

The data acquisition unit (DAS) 32 has data acquisition elements aligned in an array like the respective X-ray detection elements in the X-ray detector 26. Furthermore, the data acquisition unit (DAS) 32 acquires the X-ray beam (which is actually a detection signal) detected by the X-ray detector 26 in accordance with a data acquisition control signal output from the mount control unit 22. The acquired data is X-ray projection data.

When the rotation mount 28 rotates one revolution, the X-ray projection data is acquired for, e.g., 1000 times, and image reconfiguration is carried out based on this X-ray projection data by a predetermined method. The rotation driving unit 34 rotates the rotation mount 28 based on a mount control signal output from the mount control unit 22.

The bed driving unit 42 obtains a distance of the bed top panel 46 per revolution of the rotation mount 28 based on a bed movement signal output from the mount control unit 22, and moves the bed top panel 46 with this distance. The bed base 44 moves the bed top panel 46 in an up-and-down direction by using the bed driving unit 42. The subject P is mounted on the bed top panel 46, and the bed top panel 46 can move in a body axis direction (a Z axis direction: a slice direction) of the subject P.

The pre-processing unit 60 performs, e.g., sensitivity correction or X-ray intensity correction with respect to the X-ray projection data output from the data acquisition unit 32. The X-ray projection data subjected to processing, e.g., the sensitivity correction in the pre-processing unit 60 is temporarily stored in the projection data storage unit 62.

The reconfiguration processing unit 64 performs back projection processing with respect to the X-ray projection data stored in the projection data storage unit 62 to reconfigure image data. A method of this back projection is the same as a known method. Further, when performing interpolation processing with respect to the X-ray projection data, a known interpolation method such as a 360-degree interpolation method or a 180-degree interpolation method (an opposed data interpolation method) is used to obtain X-ray projection data at a target slice position. Furthermore, in the reconfiguration processing unit 64, reconfiguration processing is carried out simultaneously with scan in real time to generate a CT value change curve (a CT value time change curve).

The reconfigured image data is temporarily stored in the image storage unit 66 together with the CT value change curve which will be described later in detail, and then supplied to the image processing unit 68. The image processing unit 68 converts the image data into image data such as a tomographic view of an arbitrary cross section, a projection image from an arbitrary direction, or a three-dimensional image obtained by rendering processing to be output to the display device 70 by a known method based on an instruction from an operator which is input through the console input unit 54. The display device 70 displays a tomographic view or the like output from the image processing unit 68 in a monitor. Moreover, the display device 70 has a fourth input unit (not shown) which is used to perform operations in a screen thereof and constituted of operation buttons and others as will be described later.

Additionally, the image creation unit 72 is image creating means for creating an image at a later-explained set time after X-ray scan, and the post-processing unit 74 carries out post-processing using an image created by the image creation unit 72 in accordance with each region.

FIG. 2A is a view showing an example of a display screen of the display device 70.

In the drawing, a screen 80 is constituted of, e.g., a screen 82 which is used to specify a scan range when performing main scan, a screen 84 which displays an image after the scan, a monitor screen 86 at the time of the scan, a 4D scan wizard screen 90, and an operation unit 92 formed of operation buttons and others.

FIG. 2B is a view showing an example of a dialog for setting planned times as an example of the 4D scan wizard screen 90.

In this case, a CT value change curve 100, a setting line 102 for planned times, and image creation time zone setting buttons 104a, 104b, and 104c are displayed in the screen 90. The CT value change curve 100 represents how the inside of the subject is dyed with a contrast agent, and the planned time setting line 102 is set by a drag operation of, e.g., a non-illustrated mouse with respect to the CT value change curve 100. It is to be noted that three image creation time zone setting buttons 104a, 104b, and 104c are displayed in this example, but the present invention is not restricted thereto, and enabling setting a plurality of time zones can suffice. Alternatively, one time zone alone may be set. Further, an image creation time zone may be a pinpoint time zone or may be a time zone having a certain degree of width.

Meanwhile, this embodiment is constituted of processing which facilitates image creation by using the CT value change curve 100 and processing which facilitates post-processing in accordance with each region.

Figure 3:
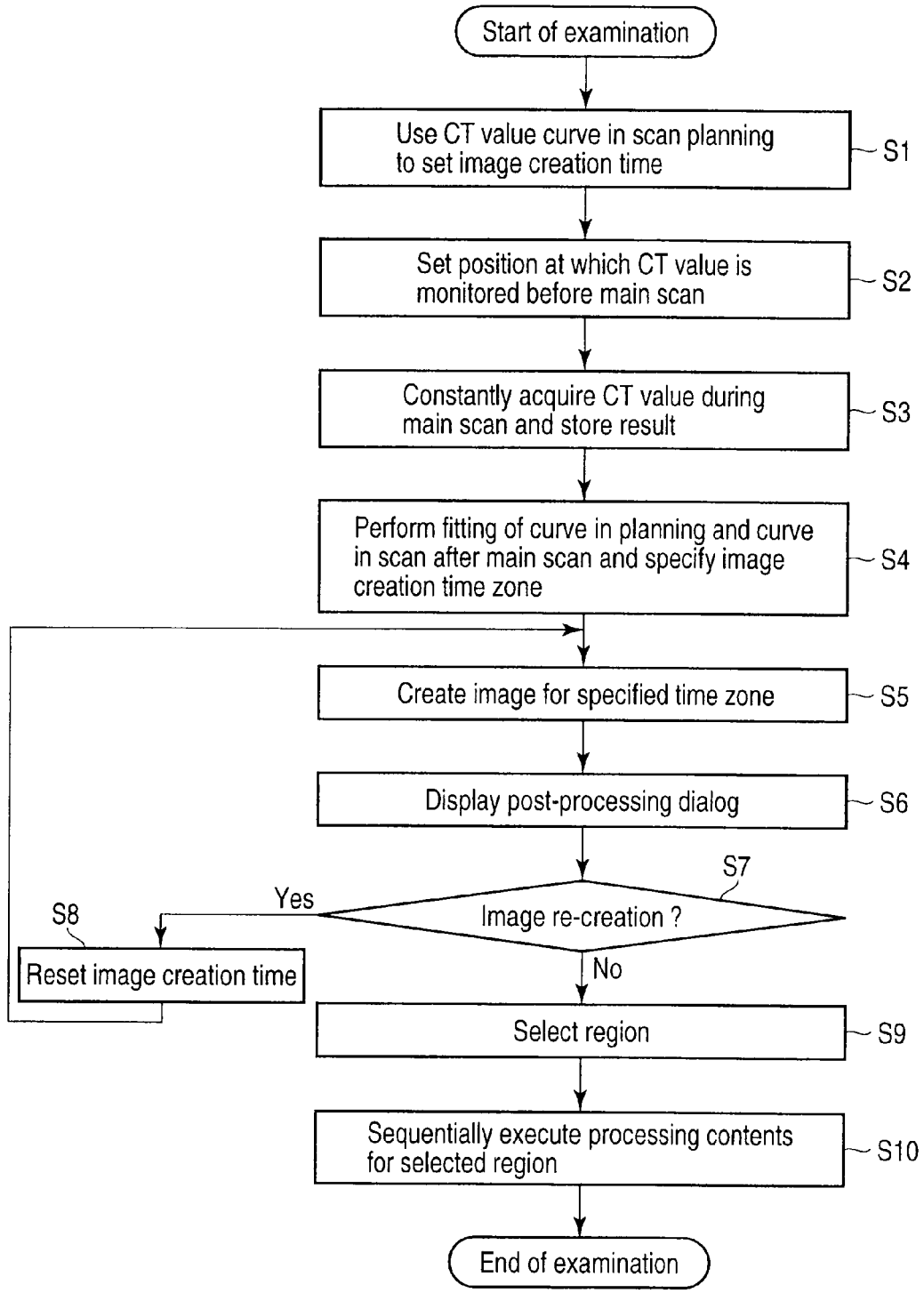
FIG. 3 is a flowchart for explaining a procedure of an examination of an X-ray CT scanner according to an embodiment of the present invention.

A procedure of examination will now be described with reference to a flowchart of FIG. 3.

First, at a step S1, a dialog of the main scan after execution of scanogram as planning imaging which is required to perform the main scan is held. Based on this dialog, a general CT value change curve is displayed, and image creation in a desired time zone is planned on this CT value change curve. The CT value change curve in this example is determined as a statistical curve calculated in accordance with, e.g., a region, an age, or a weight of the subject P.

Then, at a step S2, a CT value of a region as a monitoring target is set before the main scan. This is performed by using the screen 82 which is utilized to specify a scan range of the scanogram. Thereafter, at a step S3, the main scan is carried out, and a CT value of the set region is monitored during the main scan. Furthermore, a CT value change curve after the scan is stored in the image storage unit 66. Moreover, the reconfiguration processing is executed simultaneously with the main scan in real time to generate a time change curve of the CT value.

It is to be noted that the CT value change curve represents a value (e.g., an average, integration, or weighting addition of respective pixels) based on the CT value in a specified region of interest. Additionally, when obtaining the time change curve, the reconfiguration processing unit 64 carries out the image reconfiguration, but this processing is restricted to some of regions (a spatial region). Then, in regard to a time range specified based on this CT value change curve, a region different from the spatial region, e.g., an overall spatial region which is larger than a spatial region for the CT value change curve generating reconfiguration is reconfigured.

At a step S4, after the scan, fitting processing is performed with respect to the stored CT value change curve and the general CT value change curve which is used at the time of planning. As a result, the planned time zone is specified on the actual CT value change curve. At a subsequent step S5, an image in the planned time zone is created by the image creation unit 72 based on a result of this step S4.

FIGS. 4A to 4D are views for explaining the specification of a creation time zone based on the fitting of the CT value change curves.

Figure 4C:
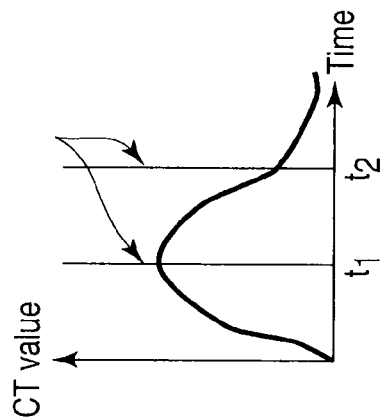
FIGS. 4A to 4D are views for explaining the specification of a crated time zone based on the fitting of CT value change curves.
Figure 4D:
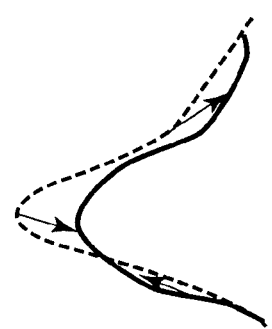
Figure 4A:
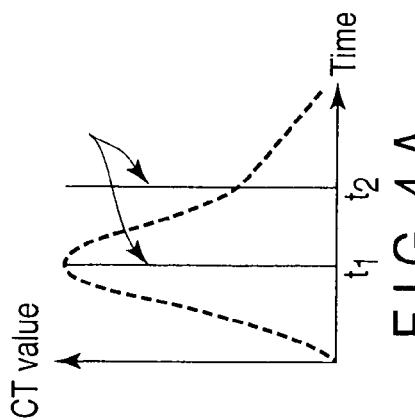
Figure 4B:
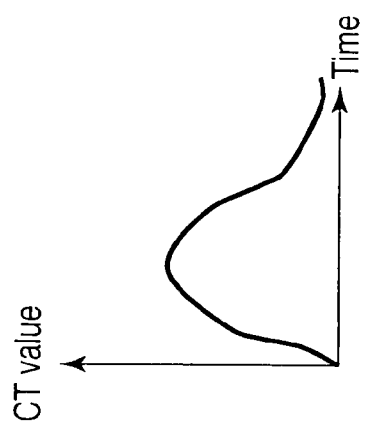

For example, a curve indicated by a broken line in FIG. 4A is the statistical curve, and time zones $t_1$ and $t_2$ are defined as time zones which should be created at the time of planning. On the other hand, FIG. 4B shows a CT value change curve obtained by the main scan for the actual subject. Further, as shown in FIG. 4C, the statistical CT value change curve depicted in FIG. 4A is combined with the CT value change curve of the main scan by, e.g., a technique such as a least-square method. As a result, as shown in FIG. 4D, the times zones $t_1$ and $t_2$ for the actual CT value change curve are specified.

Then, at a step S6, a processing dialog after execution of the main scan is displayed in the screen 90. In this dialog display, the time zone for image creation can be again specified. That is, at a step S7, whether image re-creation is performed is judged.

Figure 5:
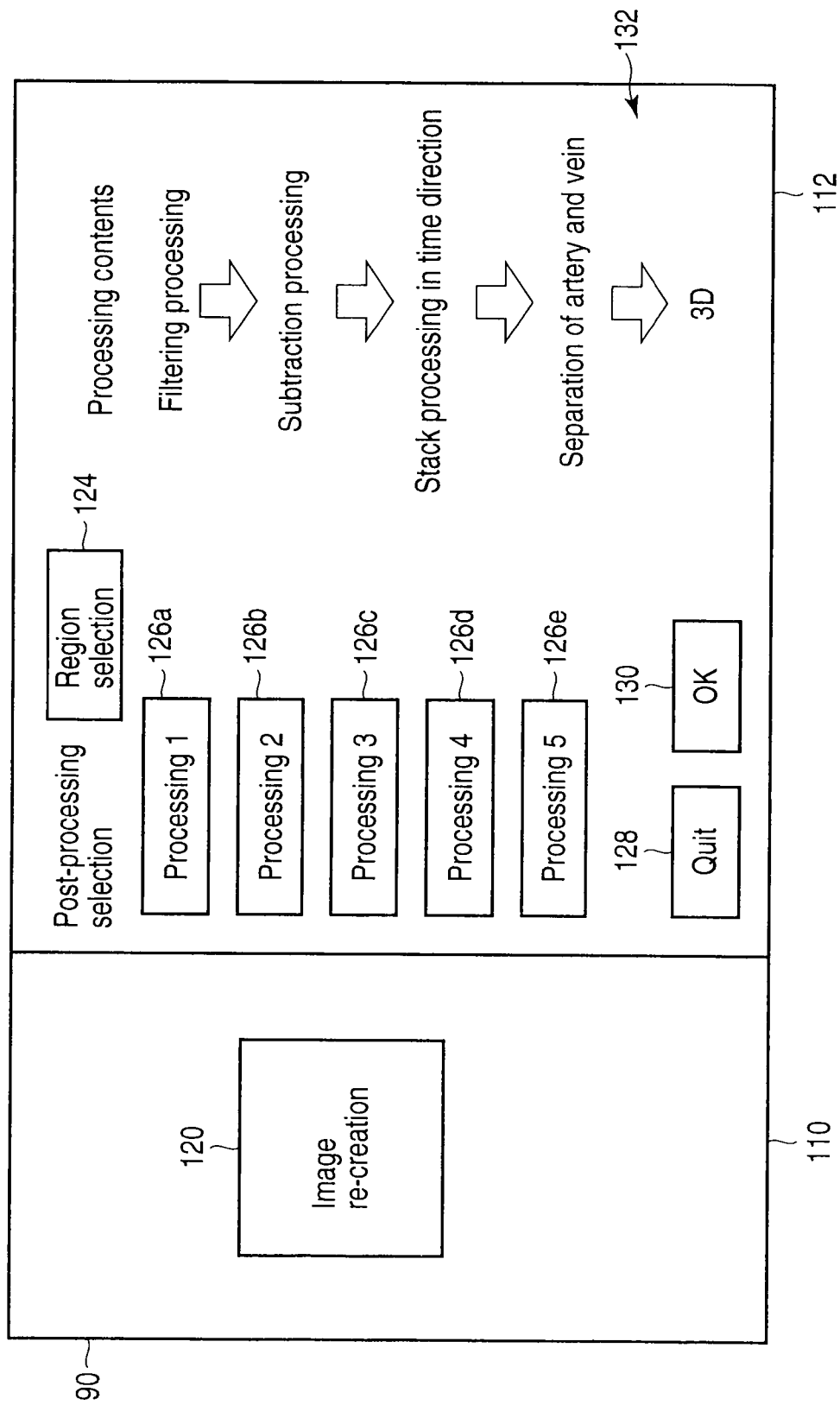
FIG. 5 is a view showing an example of a dialog for processing after scan as an example of the 4D scan wizard screen 90.

FIG. 5 is a view showing an example of a dialog for processing after the scan as an example of the 4D scan wizard screen 90. In this case, the screen 90 is constituted of an image re-creation area 110 and a post-processing dialog area 112 which is used to explain a flow of processing after the scan.

An image re-creation button 120 is displayed in the image re-creation area 110. This image re-creation button 120 is a button which is used to re-create an image when an image obtained by the processing at the steps S1 to S5 is not satisfactory for an operator, for example. That is, when the image re-creation button 120 is pressed by, e.g., a non-illustrated mouse, image re-creation is executed. In this case, the control advances to a step S8 from the step S7 to return to the display screen 80 depicted in FIG. 2 where an image creation time is reset. However, in this case, the actual CT value change curve is used. Then, the control proceeds to the step S5.

On the other hand, when the image re-creation button 120 is not pressed at the step S7, a region is selected at a step S9 so that image processing using the image can be smoothly executed.

The post-processing dialog area 112 in the screen 90 depicted in FIG. 5 is constituted of a region selection button 124, a post-processing selection button (processing 1) 126a, a post-processing selection button (processing 2) 126b, a post-processing selection button (processing 3) 126c, a post-processing selection button (processing 4) 126d, a post-processing selection button (processing 5) 126e, and a cancel button (Quit) 128 which prevents the post-processing from being executed, a selection determining OK button 130, and a processing contents display unit 132.

At the step S9, a protocol for the post-processing set in accordance with each region is selected. That is, when the region selection button 124 is operated by, e.g., the non-illustrated mouse, protocols for desired regions, e.g., a head region or a chest region are sequentially switched.

Further, after each region is selected, a dialog which is used to execute the post-processing in accordance with each selected region is displayed in the post-processing dialog area 112. Furthermore, the post-processing is sequentially executed in accordance with contents of each displayed protocol. That is, it is assumed that any one of the post-processing selection buttons 126a to 126e displayed as the processing 1 to the processing 6 in the post-processing dialog area 112 is selected and the OK button 130 is pressed to determine contents. Then, the processing contents selected from the post-processing selection buttons 126a to 126e are displayed in the processing contents display unit 132.

For example, assuming that the post-processing selection button (the processing 1) 126a is selected, the processing contents display unit 132 displays that the processing contents are "filtering processing", "subtraction processing", "stack processing in a time direction", "separation of an artery and a vein", and "3D display" in the mentioned order. As a result, processing conforming to the processing contents is executed in the post-processing unit 74. It is to be noted that, although illustrations and descriptions will be omitted, various kinds of processing contents are likewise displayed in regard to the post-processing selection buttons 126b to 126e.

It is to be noted that, when processing from the beginning to image creation is automatically executed (e.g., the filtering processing) and when 3D creation is carried out, the control may automatically advance to the dialog and then automatically proceed to the next step after termination of the processing (closing) by an operator in some cases.

Further, when the cancel button 128 is pressed, the post-processing based on the scan is not automatically effected, and the processing is manually performed.

It is to be noted that, when changing the image creation time, this change is made at the step S8 in the foregoing embodiment, but the present invention is not restricted thereto. For example, this change may be made when setting the image creation time at the step S1.

As explained above, according to the present invention, in the 4D dynamic scan, an image can be readily created in an optimum time zone. As a result, since creating each image in a desired time zone alone can suffice, an amount of image data can be reduced, and the post-processing can be effected by a simple operation. Therefore, a time from the examination to the diagnosis can be reduced, thereby improving a work flow.

Although the embodiment according to the present invention has been explained above, various modifications of the present invention can be carried out without departing from the scope of the invention besides the foregoing embodiment.

Moreover, the foregoing embodiment includes inventions on various stages, and various inventions can be extracted by appropriately combining a plurality of disclosed constituent requirements. For example, even if some of all the constituent requirements disclosed in the embodiment are deleted, the problem described in the section "problem to be solved by the invention" can be solved. When the effect described in the section "effect of the invention" can be obtained, a configuration obtained by deleting the constituent requirements can be also extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT scanner comprising:
    a setting section which sets first and second times defining a first image creation time zone in a pre-stored first CT value change curve which is a statistical representation of how the inside of a subject is dyed with a contrast agent as a function of time, the first CT value change curve having a peak;
    an X-ray tube which generates X-rays toward a subject to perform scanning after the first image creation time zone is set by the setting section;
    an X-ray detector which detects the X-ray generated by the X-ray tube and passing through the subject in which a contrast agent is injected, and converts the detected X-ray into an electric signal;
    generating section which generates a real time second CT value change curve associated with the subject based on the electric signal;
    a specifying section which combines the first CT value change curve and the second CT value change curve to specify third and fourth times defining a second image creation time zone in the second CT value change curve, the third and fourth times defining the second image creation time zone in the second CT value change curve corresponding to the first and second times defining the first image creation time zone; and
    a creating section which creates an image based on X-rays detected in the second image creation time zone.

2. The X-ray CT scanner according to claim 1, wherein the creating section is configured to create the image by using the first CT value change curve even after the X-ray scan.

3. The X-ray CT scanner according to claim 1, further comprising post-processing section for executing post-processing using the image created by the creating section in accordance with each region of the subject.

4. The X-ray CT scanner according to claim 3, further comprising a display device configured to select desired post-processing by displaying processing contents performed by the post-processing section.

5. The X-ray CT scanner according to claim 1, further comprising a display section which displays the first CT value change curve,
    wherein the setting section sets the first image creation time zone in response to input of an instruction to the displayed first CT value change curve.

6. The X-ray CT scanner according to claim 1, wherein the first CT value change curve is selectable from a plurality of CT value change curves, and
    the setting section sets the first image creation time zone by selecting a CT value change curve among the plurality of CT value change curves.

7. The X-ray CT scanner according to claim 1, wherein the specifying section performs fitting processing for the first CT value change curve and the second CT value change curve in order to specify the second image creation time zone.

8. An X-ray CT scanning method comprising:

setting first and second times defining a first image creation time zone in a pre-stored first CT value change curve which is a statistical representation of how the inside of a subject is dyed with a contrast agent as a function of time;

generating X-rays toward a subject to perform scanning after the first image creation time zone is set;

detecting the X-ray passing through a subject in which a contrast agent is injected, and converting the detected X-ray into an electric signal;

generating a real time second CT value change curve associated with the subject based on the electric signal;

combining the first CT value change curve and the second CT value change curve to determine third and fourth times defining a second image creation time zone in the second CT value change curve, the third and fourth times defining the second image creation time zone in the second CT value change curve corresponding to the first and second times defining the first image creation time zone; and creating an image based on detected X-ray detected in the second image creation time zone.

9. The method according to claim 8, wherein the first CT value change curve is a general CT value change curve.

10. The method according to claim 8, wherein the first CT value change curve has a peak.

11. The method according to claim 8, wherein the image creating step creates the image by using the first CT value change curve even after the X-ray scan.

12. The method according to claim 8, further comprising:

executing post-processing using the image created in the image creating step in accordance with each region of the subject.

13. The method according to claim 12, further comprising displaying processing contents performed during executing post-processing to select desired post-processing.

14. The method according to claim 8, further comprising:

displaying the first CT value change curve, wherein the setting step sets the first image creation time zone in response to input of an instruction to the displayed first CT value change curve.

15. The method according to claim 8, wherein the first CT value change curve is selectable from a plurality of CT value change curves, and the setting step includes selecting a CT value change curve among the plurality of CT value change curves.

16. The method according to claim 8, wherein the combining step performs fitting processing for the first CT value change curve and the second CT value change curve in order to determine the second image creation time zone.

* * * * *